US006930200B2

(12) United States Patent
 Mjalli

(10) Patent No.: US 6,930,200 B2
(45) Date of Patent: Aug. 16, 2005

(54) MULTICOMPONENT SYNTHESIS OF AMINO ACIDS AND DERIVATIVES THEREOF

(75) Inventor: Adnan M. M. Mjalli, Jamestown, NC (US)

(73) Assignee: Pharmacore, Inc., High Point, NC (US)

( * ) Notice: Subject to any disclaimer, the term of this patent is extended or adjusted under 35 U.S.C. 154(b) by 54 days.

(21) Appl. No.: 10/607,234

(22) Filed: Jun. 26, 2003

(65) Prior Publication Data

US 2004/0059149 A1 Mar. 25, 2004

Related U.S. Application Data

(62) Division of application No. 09/889,087, filed as application No. PCT/US00/01480 on Jan. 21, 2000, now abandoned.
(60) Provisional application No. 60/116,915, filed on Jan. 22, 1999.

(51) Int. Cl.$^7$ ..................... C07C 229/02; C07D 211/40; C07D 409/08; C07D 407/08
(52) U.S. Cl. ........................ 562/433; 560/19; 560/38; 560/39; 560/40; 560/45; 560/46; 560/47; 546/190; 549/13; 549/356; 549/551
(58) Field of Search ........................... 562/433; 560/19, 560/38–40, 45–47; 546/190; 549/13, 356, 551

(56) References Cited

U.S. PATENT DOCUMENTS

| 3,489,751 A | 1/1970 | Crast, Jr. |
| 3,634,418 A | 1/1972 | Willner |
| 4,535,167 A | 8/1985 | Freidinger |
| 4,631,211 A | 12/1986 | Houghten |
| 4,757,153 A | 7/1988 | Hansen, Jr. et al. |
| 5,280,093 A | 1/1994 | Jacquier et al. |

FOREIGN PATENT DOCUMENTS

| DE | 726 386 C | 10/1942 |
| DE | 36 24 376 A | 1/1988 |
| EP | 0 779 076 A | 6/1997 |
| GB | 867 572 A | 5/1961 |

OTHER PUBLICATIONS

Ugi, I. et al "MCR 6:Chiral 2,6–piperazinediones via Ugi reactions . . . " Heterocycles (1998) vol. 47, No. 2, pp 965–975.*
Stryer, Lubert, "Biochemie", 1983, Vieweg and Sohn Verlagsgesellschaft MBH, Germany XP002221913, pp. 10–14; in particular table 2–1.
Signma–Aldrich Chemie GMBH, "Biochemical and reagents for life science research", 1999, Sigma–Aldrich Co. XP002221914, pp. 90–95.
Supplementary Partial European Search Report for Application EP 00 90 8331 mailed Jan. 9, 2003.

Cao, X. et al., "Synthesis of NH–acyl–α–aminoamides on rink resin: inhibitors of the hematopoietic protein tyrosine phosphatase" Bioorg. Med. Chem. Lett. vol. 5, 1995, 2953–2958.
Demharter, A. et al. Synthesis of Chiral 1,1'—Iminodicarboxylic Acid Derivatives from—α Amino Acids Aldehydes, Isocyanides, and Alcohols by the Diastereoselective Five—Center–Four–Component Reactron. Angew. Chem. Int. Ed. Engl. 35: 173–175 (1996).
Faust, "Geminal Benzotriazolyl Ethoxy derivatives–Efficient auxiliaries in the synthesis of unsaturated carbonyl compounds", J. Prakt. Chem., 1997, vol. 339, p. 98–100.
Keating, et al., "Molecular diversity via a convertible isocyanide in the Ugi four component condensation" J. Am. Chem. Soc. 1995, vol. 117, 7842–7843.
Keating, T.A. et al. "Postcondensation Modifications of Ugi Four–Component Products: 1–Isocyanocyclohexene as a convertible Isocyanide Mechanism of Conversion, Synthesis of Diverse Structures, and Demonstration of Resin Capture" J. Am. Chem. Soc. 1996, vol. 118, p 2574–2583.
Kitaguchi et al."Enzymatic formation of an isopeptide bond involving the E–amino group of lysine" Tetrahedron Lett., 1988, vol. 29, pp. 5487–5488.
Kunz, H. et al. "Carbohydrates as chiral templates: diastereoselective Ugi synthesis of (S) amino acids using o–acylated d–arabinopyranosylamine as the auxiliary" Tetrahedron . Lett., 1989, vol. 30, pp. 4109–4110.
Linderman, "Enhanced diastereoselectivity in the asymmetric Ugi reaction using a new convertible isonitrile" J. Org. Chem., 1999, vol. 64, pp. 336–337.
Mjalli, et al., "Solid phase synthesis of pyrroles derived from a four component condensation" Tetrahedron Lett., 1996, vol. 37, pp. 2943–2946.
Siglmüller et al. "Chiral ferrocenylalkylamines from (–)–menthone" Tetrahedron, 1986, vol. 42, pp. 5931–5940.
Ugi, I., Isonitrile Chemistry, p. 1, Academic Press, New York and London, 1971.
Ugi, I., "From Isocyanides via four–component condensations to antibiotic synthesis" Angew Chem., Int. Ed. Engl., 1982, vol. 21, pp. 810–819.
Ugi, I., "Perspektiven von Multikomponentenreaktionen und deren Bibliotheken" J. Prakt. Chem., 1997, vol. 339, p. 499–516.
Ugi et al., "Die Kondensation von Carbonsauren, Aldehyden und Isonitrilen mit primaren aliphatischen Aminen, die einen abspaltbaren Alkyl–oder Alkenyl–Rest tragen" Chem. Ber., vol. 97, pp. 2996–3005 (1964).
Dömling et al. "Multicomponent Reactions with Isocyanides" *Angew. Chem. Int. Ed.,* vol. 39, pp. 3168–3210 (2000).

* cited by examiner

Primary Examiner—James O. Wilson
Assistant Examiner—Leigh C. Maier
(74) Attorney, Agent, or Firm—Kilpatrick Stockton

(57) ABSTRACT

Mono-substituted and di-substituted alpha-amino acids and derivatives thereof, substituted at the alpha positon with one (mono-) or two (di-) substituents ($R^2$ and/or $R^3$) as shown in Formula 1: $N(R^4R^5)C(R^2R^3)CO(OR^1)$.

7 Claims, No Drawings

MULTICOMPONENT SYNTHESIS OF AMINO ACIDS AND DERIVATIVES THEREOF

This application is a divisional application of pending application Ser. No. 09/889,087, filed Jul. 11, 2001 now abandoned, which is the National Stage of International Application PCT/US00/01480, filed Jan. 21, 2000, which claims the benefit of priority of U.S. Provisional Application No. 60/116,915, filed Jan. 22, 1999.

FIELD OF THE INVENTION

The present invention relates to mono-substituted and di-substituted alpha-amino acids and derivatives thereof, such as but not limited to esters, amides and salts. The alpha-amino acid compounds and their derivative compounds are substituted at the alpha position with one (mono-) or two (di-) substituents ($R^2$ and/or $R^3$) as shown in Formula 1 below:

$$N(R^4R^5)C(R^2R^3)CO(OR^1) \qquad \text{Formula 1}$$

where the moieties $R^1$, $R^2$, $R^3$, $R^4$, and $R^5$ are as defined below. Mono-substituted and di-substituted alpha-amino acids and derivatives thereof are useful, for instance, as raw materials for pharmaceutical and agro-chemical products.

| Table of Abbreviations | |
|---|---|
| Ac | acetyl |
| Alloc | allyloxycarbonyl |
| Bn | benzyl |
| BOC | tert-butyloxycarbonyl |
| CBZ | benzyloxycarbonyl |
| Et | ethyl |
| Fmoc | 9-fluorenylmethyloxycarbonyl |
| h | hour |
| IR | infrared |
| MS | mass spectroscopy |
| Me | methyl |
| mL | milliliter |
| NMR | nuclear magnetic resonance |
| OTBDMS | tert-butyl dimethyl silyl |
| Ph | phenyl |
| RT | room temperature |
| Su | succinamide |
| t-Bu | tertiary-butyl |

BACKGROUND OF THE INVENTION

As reported in the literature, a number of routes are known for the synthesis of alpha-amino acids. The best-known route is the Strecker synthesis route (see, Introduction to Organic Chemistry, Streitwieser and Heathcock, Macmillan Publishing Co., Inc. New York, 1981). In this method a suitable aldehyde is treated with ammonia and HCN, so that an alpha-amino nitrile is formed, which is subsequently subjected to a hydrolysis reaction to provide the corresponding alpha-amino acid.

Also, it has been shown (see, Ugi, I. Angew. Chem., Intl. Ed. Engl., 1982, Vol. 21, pp. 810–819, and Ugi, I. et al., J. Prokt. Chem., 1997, Vol. 339, p. 499) that the reaction of an isocyanide ($X^1NC$) with a carboxylic acid ($X^2COOH$), an aldehyde ($X^3CHO$) and an amine ($X^4NH_2$) under the appropriate conditions provided the corresponding dipeptide (N-alkyl-N-acyl-alpha amino amide) as follows:

$$X^1\text{—NC} + X^2\text{—COOH} + X^3\text{—CHO} + X^4NH_2 \rightarrow X^2\text{—CO—NX}^4\text{—CHX}^3\text{—CO—NX}^1H$$

N-alkyl-N-acyl-alpha amino amide (i.e., a dipeptide)

In an attempt to convert the dipeptides to their corresponding alpha-amino acids, Ugi used chiral ferrocenylamine in the above-mentioned reaction. The desired amino acids were obtained with low to modest diastereoselectivity. (See, Ugi I. et al., Tetrahedron Lett., 1986, Vol. 42, pp. 5931–5940).

Furthermore, the use of a convertible isocyanide in the Ugi reaction, namely cyclohexene-isocyanide, followed by hydrolysis to provide the corresponding peptide carboxylic acid, has been demonstrated (see, Armstrong, R. W. et al., J. Am. Chem. Soc., 1996, Vol. 118, p. 2574) as follows:

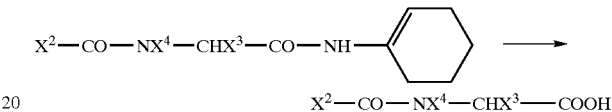

N-alkyl-N-acyl-alpha-amino acid (i.e., a peptide carboxylic acid)

In addition, the use of phenyl-isocyanide and pyridyl-isocyanide was demonstrated in the conversion of dipeptides made by Ugi into pyrrole derivatives (see, Mjalii, et al., Tet. Lett., 1996, Vol.37, pp.2943–2946).

Moreover, the use of sugar derivatives (protected galactosylamine and arabinopyranosylamine) as chiral amines with t-butyl-isocyanide converted the dipeptides made by Ugi into the corresponding sugar dipeptides, which were then converted in four chemical steps:

(1) HCl, MeOH, 0° C. to RT, 4 h;
(2) $H_2O$, 12 h, RT;
(3) 6N HCl, 80° C., 24 h; and
(4) Amberlite, IR 200 using very harsh conditions to the corresponding alpha-amino acids as shown below:

$$X^2\text{—CO—N(sugar)-CHX}^3\text{—CO—NH—C(CH}_3)_3 \rightarrow NH_3Cl\text{—CHX}^3\text{—COOH}$$

where used was an aldehyde, $X^3CHO$, where $X^3=Ph$, t-Bu, $(CH_2)_3 COOH$, Bn, or para-Cl-Ph (see, Kunz, H. et al., Tet. Lett., 1988, Vol. 29, p. 5487, and Kunz, H. et al., Tet. Lett., 1989, Vol. 30, pp. 4109–4110).

This sugar amine was also described being made by utilizing different isocyanides and then being converted in three chemical steps:

(1) HCl, MeOH, 0° C. to RT, 4 h;
(2) $H_2O$, 12 h, RT; and
(3) 2N HCl, 60° C., 24 h
as shown below:

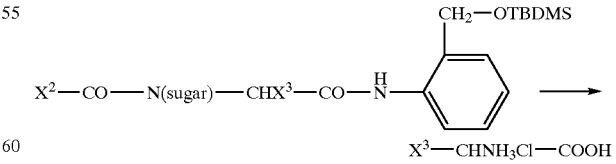

where used was an aldehyde, $X^3CHO$, where $X^3=Ph$, t-Bu, $(CH_2)_4COOH$, Bn, or $H_2C$=CH (see, Linderman, R. J., J. Am. Chem. Soc., 1999, Vol. 64, pp. 336–337).

Also, it has been reported (see, Ugi et al., Angew. Chem. Intl. Ed. Engl., 1996, Vol. 35, p.173) that the reaction of unprotected alpha-amino acids (namely valine, phenyl alanine and proline) with a series of isocyanides and aldehydes in MeOH provided the corresponding three amino peptides with excellent yield and good diastereoselectivity as shown below:

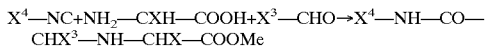

N-alkyl-N-acyl-alpha amino amide
More specifically, the synthesis of the following three compounds has been reported by this method:

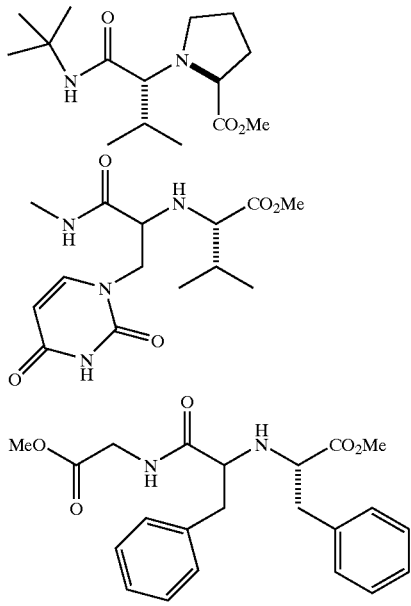

SUMMARY AND OBJECTS OF THE INVENTION

The present invention provides mono-substituted and di-substituted alpha-amino acids and derivatives thereof, such as but not limited to esters, amides and salts. The alpha-amino acids and their derivatives are of Formula 1 and are substituted at the alpha position with one or two substituents as shown below:

 Formula 1 where $R^1$, $R^2$, and $R^3$ are the same or different and are selected from:
(a) H, with the proviso that at least one of $R^2$ and $R^3$ is not H,
(b) mono-, di-, and tri-substituted aryl, and
(c) $C_1$–$C_{10}$ alkyl, $C_1$–$C_{10}$ substituted alkyl, $C_1$–$C_{10}$ substituted alkyl-aryl, $C_1$–$C_{10}$ substituted alkenyl, and $C_1$–$C_{10}$ substituted alkenyl aryl,
where the substituents of (b) and (c) are selected from:
  H, chloro, fluoro, bromo, iodo, nitro, cyano, amino, $C_1$–$C_{10}$ alkyloxy, $C_1$–$C_{10}$ alkyloxy aryl, $C_1$–$C_{10}$ aminoalkyl, $C_1$–$C_{10}$ alkylamino, $C_1$–$C_{10}$ aminoalkyl aryl, $C_1$–$C_{10}$ aminocarbonyl, $C_1$–$C_{10}$ aminocarbonylalkyl-aryl, $C_1$–$C_{10}$ thioalkyl, $C_1$–$C_{10}$ thioalkyl-aryl, $C_1$–$C_{10}$ alkylsulfoxide, $C_1$–$C_{10}$ alkylsulfone, $C_1$–$C_{10}$ alkylsulfonamide, $C_1$–$C_{10}$ alkylsulfonamide aryl, $C_1$–$C_{10}$ alkylsulfoxide aryl, $C_1$–$C_{10}$ alkylsulfone aryl, $C_1$–$C_{10}$ alkyl, aminocarbonylamino $C_1$–$C_{10}$ alkyl, $C_1$–$C_{10}$ alkyl aminocarbonylamino $C_1$–$C_{10}$ alkyl aryl, $C_1$–$C_{10}$ alkyloxycarbonyl $C_1$–$C_{10}$ alkyl, $C_1$–$C_{10}$ alkyloxycarbonyl $C_1$–$C_{10}$ alkyl aryl, $C_1$–$C_{10}$ carboxyalkyl, $C_1$–$C_{10}$ carboxyalkyl aryl, $C_1$–$C_{10}$ carbonylalkyl, $C_1$–$C_{10}$ carbonylalkyl aryl, $C_1$–$C_{10}$ alkyloxycarbonylamino alkyl, $C_1$–$C_{10}$ alkyloxycarbonylamino alkyl aryl, guanidino, $C_1$–$C_{10}$ alkylCOOH, $C_1$–$C_{10}$ alkylCONH$_2$, $C_1$–$C_{10}$ alkenylCOOH, $C_1$–$C_{10}$ alkenyl CONH$_2$, and
where the aryl group of (b) and (c) is selected from:
  phenyl, biphenyl, 2-napthyl, 1-napthyl, pyridyl, furyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, isoindolyl, purinyl, carbazolyl, isoxazolyl, thiazolyl, oxazolyl, benthiazolyl, benzoxazolyl; and
where $R^4$ and $R^5$ are the same or different and are selected from:
(d) H, and
(e) an amine protecting group.

The present invention also provides for a method for the synthesis of compounds of Formula 1, where $R^1$, $R^2$, $R^3$, $R^4$, and $R^5$ are as defined above, by reacting (1) a suitable carbonyl compound, such as an aldehyde or a ketone, (2) an amino acid (employed as an amino acid/removable chiral auxiliary), and (3) a convertible isocyanide using appropriate reaction conditions to provide compounds Formula 2 below:

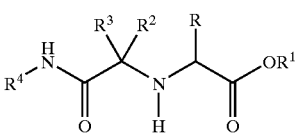 Formula 2 that are then subjected in situ, or after isolation and purification, to mild amide hydrolysis or cleavage to provide compounds of Formula 1 as racemates or in optically pure form. More particularly, the method comprises:
(i) reacting an amino acid/removable chiral auxiliary or salt thereof, a convertible isocyanide, and at least one of an aldehyde and a ketone, in an alcohol or alcohol-containing solvent to obtain a compound of Formula 2

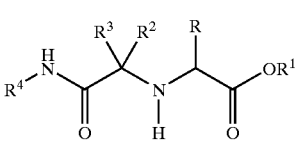 Formula 2 and (ii) subjecting the compound of Formula 2 to aryl amine cleavage/hydrolysis, including catalytic hydrogenation, and to amide cleavage/hydrolysis to obtain the compound of Formula 1, and preferably, step (ii) comprises that the aryl amine cleavage/hydrolysis and the amide cleavage/hydrolysis are followed by an amine protection reaction to place at least one amine protection group on the N of Formula 1.

Hence, it is an object of the invention to provide certain novel alpha-amino acids.

Some of the objects of the invention having been stated above, other objects will become evident as the description proceeds, when taken in connection with the Laboratory Examples as best described below.

DETAILED DESCRIPTION OF THE INVENTION

The present invention involves the preparation of mono-substituted and di-substituted alpha-amino acids and their derivatives as shown in Formula 1 below:

$$N(R^4R^5)C(R^2R^3)CO(OR^1) \quad \text{Formula 1}$$

where the alpha-amino acids and their derivatives may be N-protected with a substituent, such as but not limited to tert-butyloxycarbonyl (BOC), 9-fluorenylmethyloxycarbonyl (Fmoc), allyloxycarbonyl (Alloc), butyloxycarbonyl (CBZ) and salts thereof, as represented in Formula 1 by $R^4$ and $R^5$. The alpha position is substituted with one or two substituents, as represented in Formula 1 by $R^2$ and $R^3$. The nature of the starting carbonyl (aldehyde or ketone) compounds selected determines the nature of the desired alpha-amino acid (mono-, di-, cyclic and acyclic) substituents, $R^2$ and $R^3$. The acid functionality, as represented by $R^1$ in Formula 1, may be H or may be a suitable functional group to provide derivatives such as but not limited to esters, amides, and salts, as represented by $R^1$ in Formula 1.

The process according to the invention is technically simple and economically attractive. With the process according to the invention, high yields are obtained with a minimal number of chemical steps. Also, the process according to the invention not only provides a wide range of currently available amino acids and derivatives, but also provides new amino acids and derivatives.

An amino acid/chiral auxiliary component is used in a reaction with a carbonyl compound (a ketone or an aldehyde) and an isocyanide to provide compounds as shown in Formula 2 below:

$$N(HR^4)C(O)C(R^2R^3)N(H)C(HR)C(O)(OR^1) \quad \text{Formula 2}$$

that can be converted (by cleavage/hydrolysis and amine protection) to compounds of Formula 1. Both the isocyanide portion represented by $R^4$—NH in Formula 2 and the amino acid/removable chiral auxiliary portion represented by NHC(HR)COOR$^1$ in Formula 2 are converted stepwise in any order or concurrently under mild conditions (such as but not limited to strong acid, catalytic hydrogenation, electron transfer reactions, basic conditions, or nucleophilic additions) to provide the corresponding alpha-amino acids and their derivatives as shown in Formula 1.

Moreover, besides racemates, synthesis of an enantiomerically pure compound can result from the amino acid/removable chiral auxiliary being a chiral inducer chemically to provide a majority of a single isomer of a compound of Formula 2. The major isomer can then be separated using standard chromatography techniques or crystallization prior to hydrolysis of both residues (the isocyanide and the chiral auxiliary) to provide an enantiomerically pure compound of Formula 2. After cleavage of the isocyanide and amino acid/removable chiral auxiliary portions, an enantiomerically pure compound of Formula 1 is obtained. Alternatively, the amino acid/removable chiral auxiliary can create two diastereomers of various or similar ratios of a compound of Formula 2. The diastereomers can then be separated using standard chromatography techniques or crystallization prior to hydrolysis of both residues (the isocyanide and the chiral auxiliary moieties) to provide an enantiomerically pure compound of Formula 2. The enantiomerically pure compound of Formula 2 then can be converted separately to an optically pure compound of Formula 1 upon the removal of both residues (the isocyanide and the chiral auxiliary).

More particularly, the present invention provides compounds of Formula 1

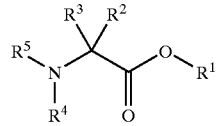

Formula 1 where:

$R^1$, $R^2$, and $R^3$ are the same or different and are selected from:

(a) H, with the proviso that at least one of $R^2$ and $R^3$ is not H, (b) mono-, di- and tri-substituted aryl, and (c) $C_1$–$C_{10}$ alkyl, $C_1$–$C_{10}$ substituted alkyl, $C_1$–$C_{10}$ substituted alkyl-aryl, $C_1$–$C_{10}$ substituted alkenyl, and $C_1$–$C_{10}$ substituted alkenyl aryl, where the substituents of (b) and (c) are selected from:

H, chloro, fluoro, bromo, iodo, nitro, cyano, amino, $C_1$–$C_{10}$ alkyloxy, $C_1$–$C_{10}$ alkyloxy aryl, $C_1$–$C_{10}$ aminoalkyl, $C_1$–$C_{10}$ alkylamino, $C_1$–$C_{10}$ aminoalkyl aryl, $C_1$–$C_{10}$ aminocarbonyl, $C_1$–$C_{10}$ aminocarbonylalkyl-aryl, $C_1$–$C_{10}$ thioalkyl, $C_1$–$C_{10}$ thioalkyl-aryl, $C_1$–$C_{10}$ alkylsulfoxide, $C_1$–$C_{10}$ alkylsulfone, $C_1$–$C_{10}$ alkylsulfonamide, $C_1$–$C_{10}$ alkylsulfonamide aryl, $C_1$–$C_{10}$ alkylsulfoxide aryl, $C_1$–$C_{10}$ alkylsulfone aryl, $C_1$–$C_{10}$ alkyl, aminocarbonylamino $C_1$–$C_{10}$ alkyl, $C_1$–$C_{10}$ alkyl aminocarbonylamino $C_1$–$C_{10}$ alkyl aryl, $C_1$–$C_{10}$ alkyloxycarbonyl $C_1$–$C_{10}$ alkyl, $C_1$–$C_{10}$ alkyloxygarbonyl $C_1$–$C_{10}$ alkyl aryl, $C_1$–$C_{10}$ carboxyalkyl, $C_1$–$C_{10}$ carboxyalkyl aryl, $C_1$–$C_{10}$ carbonylalkyl, $C_1$–$C_{10}$ carbonylalkyl aryl, $C_1$–$C_{10}$ alkyloxycarbonylamino alkyl, $C_1$–$C_{10}$ alkyloxycarbonylamino alkyl aryl, guanidino, $C_1$–$C_{10}$ alkylCOOH, $C_1$–$C_{10}$ alkylCONH$_2$, $C_1$–$C_{10}$ alkenylCOOH, $C_1$–$C_{10}$ alkenyl CONH$_2$, and the like, and where the aryl group of (b) and (c) is selected from:

phenyl, biphenyl, 2-napthyl, 1-napthyl, pyridyl, furyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, isoindolyl, purinyl, carbazolyl, isoxazolyl, thiazolyl, oxazolyl, benthiazolyl, benzoxazolyl, and the like, and where:

$R^4$ and $R^5$ are the same of different and are selected from:

H and an amine protecting group such as but not limited to phenyl, cyclohexenyl, cyclohexyl, t-butyl, Fmoc, BOC, Alloc, CBZ and the like.

Optionally, $R^2$ and $R^3$ in Formula 1 are joined together to form cyclic compounds of Formula 1a with a ring size of 3–8 as follows:

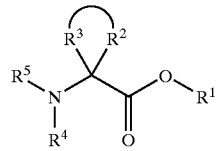

Formula 1a

For instance, the ring system may be selected from substituted-cyclopropyl, cyclobutyl, cyclopentyl, cyclohexyl, cycloheptyl, and cyclooctyl as shown in compounds of Formulae 1b and 1c as follows:

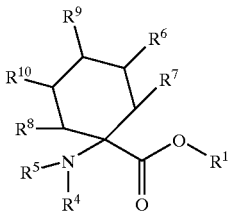

Formula 1b

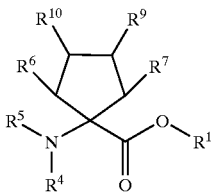

Formula 1c selected from substituted-cyclopropenyl, cyclobutenyl, cyclopentenyl, cyclohexenyl, cycloheptenyl and cyclooctenyl as in compounds of Formula 1d as follows:

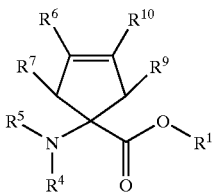

Formula 1d where $R^6$ and $R^7$, $R^6$ and $R^{10}$, or $R^9$ and $R^{10}$ may be joined together as a ring to form a fused system with the cyclopentene ring, where the aryl and its substituents are as defined below vis-à-vis (e) and (f), or selected from substituted heterocyclic compounds, where A is O, S, SO, $SO_2$, NH, $SO_2NHR^8$, $NCONHR^8$, $NCOOR^8$, or $NR^8$ inserted in the ring systems as in compounds of Formulae 1e and 1f as follows:

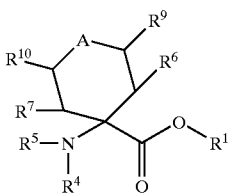

Formula 1e

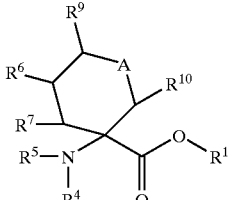

Formula 1f where the substituents $R^4$ and $R^5$ in Formulae 1a–1f are as defined above and where the substituents ($R^6$, $R^7$, $R^8$, $R^9$, and $R^{10}$) in Formulae 1a–1f are the same or different and are selected from:

(d) H,
(e) mono-, di-, and tri-substituted aryl, and
(f) $C_1$–$C_{10}$ substituted alkyl, $C_1$–$C_{10}$ substituted alkylaryl, $C_1$–$C_{10}$ substituted alkenyl, and $C_1$–$C_{10}$ substituted alkenyl aryl, where the substituents of (e) and (f) are selected from:

H, chloro, fluoro, bromo, iodo, nitro, cyano, amino, $C_1$–$C_{10}$ alkyloxy, $C_1$–$C_{10}$ alkyloxy aryl, $C_1$–$C_{10}$ aminoalkyl, $C_1$–$C_{10}$ alkylamino, $C_1$–$C_{10}$ aminoalkyl aryl, $C_1$–$C_{10}$ aminocarbonyl, $C_1$–$C_{10}$ aminocarbonylalkyl-aryl, $C_1$–$C_{10}$ thioalkyl, $C_1$–$C_{10}$ thioalkyl-aryl, $C_1$–$C_{10}$ alkylsulfoxide, $C_1$–$C_{10}$ alkylsulfone, $C_1$–$C_{10}$ alkylsulfonamide, $C_1$–$C_{10}$ alkylsulfonamide aryl, $C_1$–$C_{10}$ alkylsulfoxide aryl, $C_1$–$C_{10}$ alkylsulfone aryl, $C_1$–$C_{10}$ alkyl, aminocarbonylamino $C_1$–$C_{10}$ alkyl, $C_1$–$C_{10}$ alkyl aminocarbonylamino $C_1$–$C_{10}$ alkyl aryl, $C_1$–$C_{10}$ alkyloxycarbonyl $C_1$–$C_{10}$ alkyl, $C_1$–$C_{10}$ alkyloxycarbonyl $C_1$–$C_{10}$ alkyl aryl, $C_1$–$C_{10}$ carboxyalkyl, $C_1$–$C_{10}$ carboxyalkyl aryl, $C_1$–$C_{10}$ carbonylalkyl, $C_1$–$C_{10}$ carbonylalkyl aryl, $C_1$–$C_{10}$ alkyloxycarbonylamino alkyl, $C_1$–$C_{10}$ alkyloxycarbonylamino alkyl aryl, guanidino, $C_1$–$C_{10}$ alkylCOOH, $C_1$–$C_{10}$ alkylCONH$_2$, $C_1$–$C_{10}$ alkenylCOOH, $C_1$–$C_{10}$ alkenyl CONH$_2$, and the like, and where the aryl group of (e) and (f is selected from:

phenyl, biphenyl, 2-napthyl, 1-napthyl, pyridyl, furyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, isoindolyl, purinyl, carbazolyl, isoxazolyl, thiazolyl, oxazolyl, benthiazolyl, benzoxazolyl, and the like.

The invention relates to a synthesis where a convertible isocyanide, such as but not limited to cyclohexenyl, t-butyl, cyclohexyl, or phenyl, is used in conjunction with an appropriate "chiral auxiliary" as an amino acid input (amino acid/removable chiral auxiliary) in the three component condensation reaction to provide (after hydrolysis of both the amine and isocyanide moieties) the corresponding alpha-amino acids and their derivatives as represented by Formula 1.

Compounds of Formula 1 are synthesized according to the following reaction mechanism:

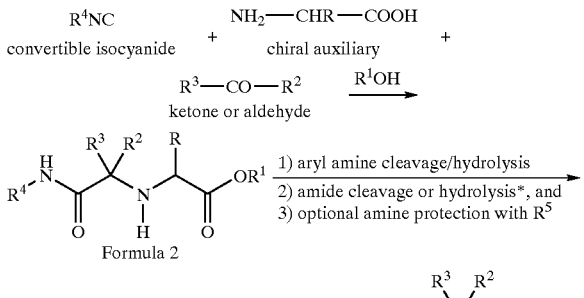

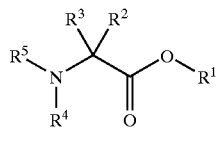

Formula 1

*It is noted that when proceeding from Formula 2 to Formula 1, 1) may be performed prior to 2), 2) may be performed prior to 1), or 1) and 2) may be performed concurrently.

Reaction of an appropriate aldehyde or ketone (such as but not limited to phenyl-acetaldehyde or cyclohexanone) with an amino acid/removable chiral auxiliary or salt thereof (such as but not limited to phenyl glycine, i.e., R is phenyl) and an appropriate convertible isocyanide (such as but not limited to $R^4$ is phenyl-, cyclohexenyl-, cyclohexyl-, or t-butyl-) utilizing an appropriate solvent and reaction conditions (such as but not limited to R¹OH is methanol, ethanol, or isopropanol, at about −80° C. to 220° C.) provided compounds of Formula 2. Then, after cleavage of both the chiral auxiliary amine and the amide portions, compounds of Formula 2 provided the corresponding alpha-amino acids and their derivatives of Formula 1.

The desired alpha-amino acid of Formula 2 has a removable amino acid/chiral auxiliary and preferably is selected from compounds where R is mono, di-, tri-, tetra- or penta-substituted aryl, where the aryl is selected from: phenyl, biphenyl, 2-naphtyl, 1-naphtyl, and the like, and the subsbtuents are selected from: H, cyano, amino, $C_1$–$C_{10}$ alkyl, $C_1$–$C_{10}$ alkyloxy, $C_1$–$C_{10}$ alkyloxy aryl, $C_1$–$C_{10}$ aminoalkyl, $C_1$–$C_{10}$ alkylamino, $C_1$–$C_{10}$ aminoalkyl aryl, and the like.

As shown in the Laboratory Examples below, compounds of Formula 2 were separated using standard separation techniques, such as but not limited to chromatography separation and crystallization, to provide enantiomerically pure compounds of Formula 2. Then, the enantiomerically pure compounds of Formula 2 were subjected to amide cleavage conditions, such as but not limited to acidic reaction conditions, such as HCl/MeOH or aqueous HCl, to provide the corresponding acid, followed by benzyl amine or derivative cleavage conditions, such as but not limited to a catalytic hydrogenation reaction, such as but not limited to $H_2$ with $Pd(OH)_2$ on carbon, to provide the corresponding amine, followed by acidic hydrolysis such as HCl/methanol or aqueous HCl to provide the corresponding enantiomerically pure amino acids of Formula 1.

Compounds were synthesized in accordance with the following Laboratory Examples.

LABORATORY EXAMPLES

Example I

Preparation of Intermediary Compound of Formula 2

Several compounds of Formula 2, where $R^1$ was Me, were synthesized according to Scheme 1 as follows:

Scheme 1

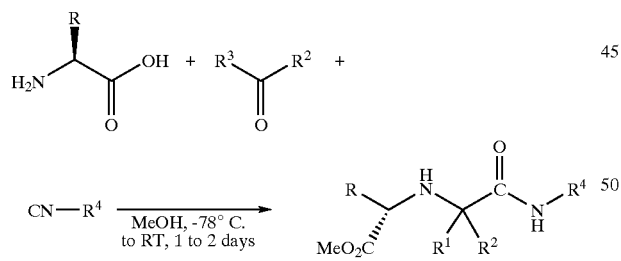

Formula 2

General Procedure

To a cooled mixture of an amino acid (1 mmol) in methanol (8 mL), at −78° C., was added an aldehyde or a ketone (1 mmol in 1 mL of MeOH) and an isocyanide (1 mmol in 1 mL MeOH). Each respective resulting mixture was allowed to warm to room temperature or reflux and stir between 3 h to 48 h. The crude reaction for each was concentrated and dissolved in 10 ml of $Et_2O$. After filtration (to remove the remaining amino acid), each respective filtrate was concentrated and purified by column chromatography on silica gel, resulting in the following compounds of Formula 2:

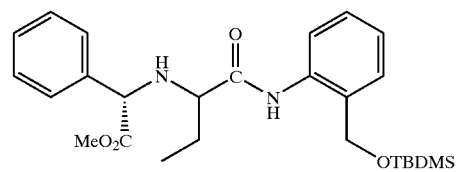

84% yield (at 92% conversion), ratio 3:2. MS (ESP+) m/z 471.20, (MH⁺) 493.16 (M+Na).

H1 NMR (CD₃OD, 300 MHz, major diastereoisomer): δ 7.77 (dd, 1H), 7.45–7.10 (m, 8H), 4.84 (d, 1H, 13.3 Hz), 4.72 (d, 1H, 13.3 Hz), 4.47 (s, 1H), 3.64 (s, 3H), 2.95 (t, 1H, 6.4 Hz), 1.73 (dq, 2H), 0.95 (t, 3H, 7.4 Hz), 0.88 (s, 9H), 0.08 (s, 3H), 0.03 (s, 3H).

H1 NMR (CD₃OD, 300 MHz, minor diastereoisomer): δ 7.77 (dd, 1H), 7.45–7.10 (m, 8H), 4.60 (d, 1H, 13.3 Hz), 4.52 (d, 1H, 13.3 Hz), 4.41 (s, 1H), 3.69 (s, 3H), 3.16 (t, 1H, 6.4 Hz), 1.83 (dq, 2H), 1.05 (t, 3H, 7.4 Hz), 0.81 (s, 9H), −0.02 (s, 3H), −0.07 (s, 3H).

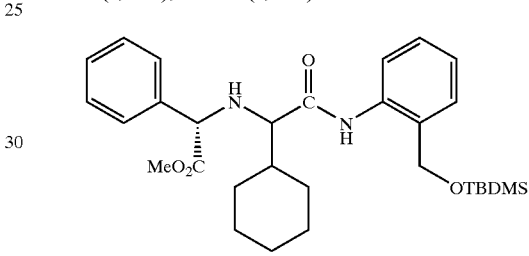

70% yield, ratio 2:1. MS (ESP+) m/z 525.37 (MH⁺).

H1 NMR (CD₃OD, 300 MHz, major diastereoisomer): δ 7.75 (dd, 1H), 7.42–7.10 (m, 8H), 4.85 (d, 1H, 13 Hz), 4.72 (d, 1H, 13 Hz), 4.40 (s, 1H), 3.64 (s, 3H), 2.79 (d, 1H, 5.9 Hz), 1.9–1.5 (m, 1H), 0.88 (s, 9H), 0.09 (s, 3H), 0.03 (s, 3H).

H1 NMR (CD₃OD, 300 MHz, minor diastereoisomer): δ 7.77 (dd, 1H), 7.45–7.10 (m, 8H), 4.56 (d, 1H, 13 Hz), 4.50 (d, 1H, 13 Hz), 4.36 (s, 1H), 3.68 (s, 3H), 3.03 (d, 1H, 5.9 Hz), 1.9–1.5 (m, 1H), 1.05 (t, 3H), 0.82 (s, 9H), −0.02 (s, 3H), −0.06 (s, 3H).

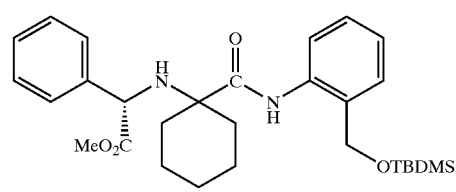

75% yield (at 93% conversion). MS (ESP+) m/z 511.71 (MH⁺).

H1 NMR (CD₃OD, 300 MHz): δ 7.66 (dd, 1H, 8.6–1.3 Hz), 7.39 (dd, 2H, 7.7–2 Hz), 7.31–7.17 (m, 5H), 7.06 (dt, 1H, 7.7–1.3 Hz), 4.49 (d, 1H, 13 Hz), 4.40 (s, 1H), 4.28 (d, 1H, 13 Hz), 3.58 (s, 3H), 2.1–1.3 (m, 10H), 0.89 (s, 9H), 0.05 (s, 3H), 0.03 (s, 3H).

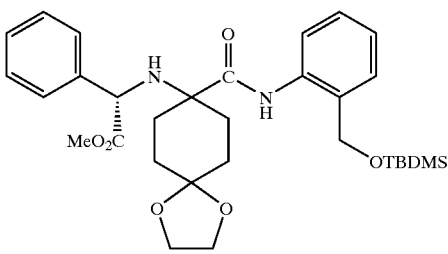

88% yield. MS (ESP+) m/z 569.71. (MH+) 591.21 (M+Na).
H1 NMR (CD₃OD, 300 MHz): δ 7.67 (dd, 1H, 8.8–1.5 Hz), 7.40 (dd, 2H, 7.8–1.8 Hz), 7.32–7.20 (m, 5H), 7.08 (dt, 1H, 7.6–1.3 Hz), 4.53 (d, 1H, 13.5 Hz), 4.38 (s, 1H), 4.36 (d, 1H, 13.5 Hz), 3.90 (s, 2H), 3.59 (s, 3H), 2.19 (m, 1H), 2.04 (m, 1H), 1.90–1.48 (m, 6H), 0.89 (s, 9H), 0.06 (s, 3H), 0.03 (s, 3H).

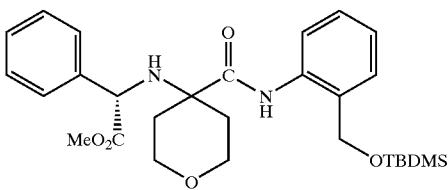

71% yield (at 69% conversion). MS (ESP+) m/z 513.68 (MH+). H1 NMR (CD₃OD, 300 MHz): δ 7.67 (dd, 1H, 8.5–1.5 Hz), 7.41 (dd, 2H, 7.9–1.9 Hz), 7.33–7.21 (m, 5H), 7.10 (dt, 1H, 7.6–1.4 Hz), 4.54 (d, 1H, 13.2 Hz), 4.43 (s, 1H), 4.37 (d, 1H, 13.2 Hz), 3.9–3.55 (m, 4H), 3.60 (s, 3H), 2.25–1.65 (m, 4H), 0.88 (s, 9H), 0.05 (s, 3H), 0.03 (s, 3H).

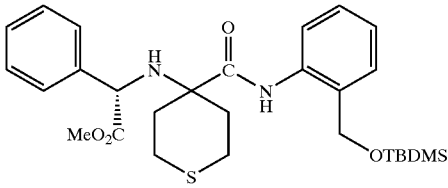

99% yield (at 53% conversion). MS (ESP+) m/z 529.43 (MH+), 551.17 (M+Na). H1 NMR (CD₃OD, 300 MHz): δ 7.67 (dd, 1H, 8.8–1.6 Hz), 7.41 (dd, 2H, 7.7–1.9 Hz), 7.33–7.20 (m, 5H), 7.09 (dt, 1H, 7.6–1.4 Hz), 4.53 (d, 1H, 13.4 Hz), 4.41 (s, 1H), 4.36 (d, 1H, 13.4 Hz), 3.60 (s, 3H), 3–2.8 (m, 2H), 2.78–2.55 (m, 2H), 2.5–2.15 (m, 2H), 2.05–1.8 (m, 2H), 0.89 (s, 9H), 0.06 (s, 3H), 0.04 (s, 3H).

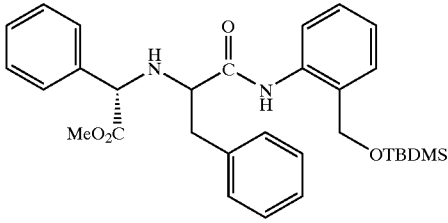

75% yield, ratio 2:1. H1 NMR (CDCl₃, 300 MHz, major diastereoisomer): δ 8.21 (d, 1H), 7.36–7.03 (m, 13H), 6.88 (dd, 1H), 4.77 (d, 1H, 12.9 Hz), 4.60 (d, 1H, 12.9 Hz), 4.35 (br d, 1H, 9 Hz), 3.61 (s, 3H), 3.24 (dd, 1H), 3.17 (dd, 1H), 2.74 (dd, 1H), 2.64 (br d, 1H), 0.89 (s, 9H), 0.07 (s, 3H), −0.02 (s, 3H). MS (ESP+) m/z 533.69 (MH+), 555.21 (M+Na).

H1 NMR (CD₃OD, 300 MHz, minor diastereoisomer): δ 8.15 (d, 1H), 7.37–7.11 (m, 12H), 7.11 (dd, 1H), 7.03 (td, 1H), 4.42 (d, 1H, 13.7 Hz), 4.33 (d, 1H, 13.7 Hz), 4.30 (br, 1H), 3.56 (s, 3H), 3.50 (dd, 1H), 3.28 (dd, 1H), 2.95 (dd, 1H), 2.66 (br, 1H), 0.80 (s, 9H), −0.06 (s, 3H), −0.12 (s, 3H). MS (ESP+) m/z 533.70 (MH+), 555.18 (M+Na).

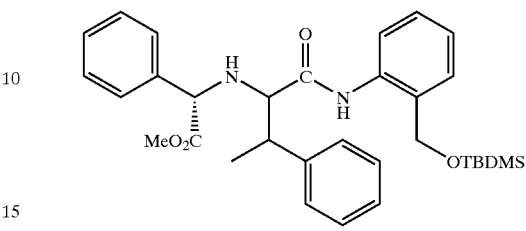

88% yield (at 85% conversion). MS (ESP+) m/z 547.70 (MH+), 569.22 (M+Na). H1 NMR (CDCl3, 300 MHz, mixture of diastereoisomers 2:2:1): δ 7.98, 7.83 and 7.76 (d, 1H), 7.61, 7.50 and 7.42 (d, 1H), 7.35–6.88 (m, 12H), 4.76 and 4.64 (d, 2H), 4.44 (d, 1H), 4.31, 4.26, and 4.14 (s, 1H), 3.59 and 3.56 (s, 3H), 3.34 (m, 1H), 1.45 and 1.38 (d, 3H), 0.92, 0.89 and 0.85 (s, 9H), 0.11, 0.10 and 0.01 (s, 3H), 0.05, 0.03 and −0.02 (s, 3H).

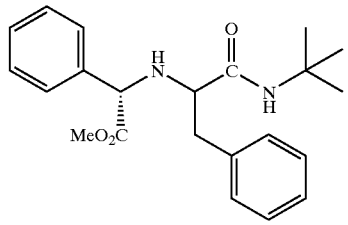

quantitative yield, ratio 7:3. MS (ESP+) m/z 369.24 (MH+), 391.21 (M+Na).
H1 NMR (CDCl3, 300 MHz, major diastereoisomer): δ 7.36–7.13 (m, 8H), 6.87 (d, 2H), 4.11 (s, 1H), 3.55 (s, 3H), 3.24 (dd, 1H, 9.9–4.2 Hz), 3.18 (dd, 1H, 13.6–4.2 Hz), 2.80 (dd, 1H, 13.6–9.9 Hz), 1.19 (s, 9H).
H1 NMR (CD₃OD, 300 MHz, minor diastereoisomer): δ 7.36–7.13 (m, 8H), 7.08 (d, 2H), 4.14 (s, 1H), 3.62 (s, 3H), 3.12 (dd, 1H, 13.6–4.2 Hz), 2.97 (dd, 1H, 9.9–4.2 Hz), 2.63 (dd, 1H, 13.6–9.9 Hz), 1.36 (s, 9H).

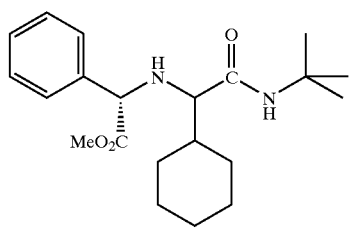

79% yield, ratio 2:1. MS (ESP+) m/z 361.65 (MH+), 383.14 (M+Na).
H1 NMR (CD₃OD, 300 MHz, major diastereoisomer): δ 7.74 (d, 2H), 7.42–7.10 (m, 7H), 4.85 (d, 1H, 13 Hz), 4.72 (d, 1H, 13 Hz), 4.40 (s, 1H), 3.64 (s, 3H), 2.79 (d, 1H, 5.9 Hz), 1.72 (m, 11H), 0.88 (s, 9H), 0.09 (s, 3H), 0.03 (s, 3H).
H1 NMR (CD₃OD, 300 MHz, minor diastereoisomer): δ 7.76 (d, 2H), 7.42–7.10 (m, 7H), 4.56 (d, 1H, 13 Hz), 4.50 (d, 1H, 13 Hz), 4.36 (s, 1H), 3.68 (s, 3H), 3.03 (d, 1H, 5.9 Hz), 1.72 (m, 11H), 0.82 (s, 9H), −0.02 (s, 3H), −0.06 (s, 3H).

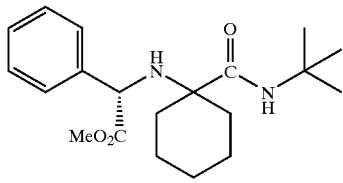

77% yield (at 40% conversion).

H1 NMR (CDCl3, 300 MHz): δ 7.42–7.27 (m, 5H), 4.22 (s, 1H), 3.66 (s, 3H), 2.94 (br s, 1H), 2.33 (m, 1H), 2.07 (m, 1H), 1.90–1.20 (m, 8H), 1.02 (s, 9H). MS (ESP+) m/z 347.64 (MH+), 369.17 (M+Na).

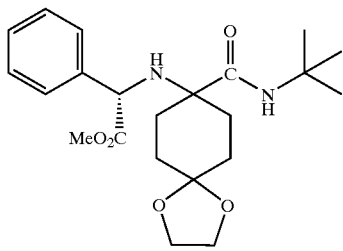

81% yield (at 64% conversion).

H1 NMR (CDCl3, 300 MHz): δ 7.40–7.26 (m, 5H), 6.60(br s, 1H), 3.90 (m, 4H), 3.64 (s, 3H), 2.50 (t, 2H, 6.9 Hz), 2.00 (t, 2H, 6.9 Hz), 1.62 (m, 4H), 1.06 (s, 9H). MS (ESP+) m/z 405.68.

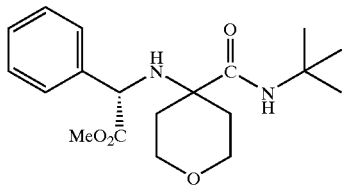

77% yield (at 50% conversion).

H1 NMR (CDCl3, 300 MHz): δ 7.42–7.35 (m, 5H), 6.61 (s, 1H), 4.25 (s, 1H), 3.93 (m, 2H), 3.68 (m, 2H), 3.67 (s, 3H), 2.30 (ddd, 1H), 1.98 (ddd, 1H), 1.57–1.42 (2H), 1.07 (s, 9H). MS (ESP+) m/z 349.19 (MH+), 371.17 (M+Na).

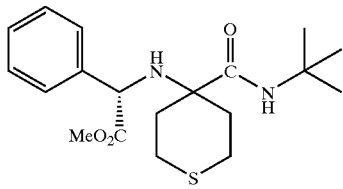

quantitative yield (at 40% conversion).

H1 NMR (CDCl3, 300 MHz) δ 7.4–7.27 (m, 5H), 6.54 (br s, 1H), 4.23 (s, 1H), 3.67 (s, 3H), 2.85 (m, 2H), 2.58 (m, 2H), 2.40 (m, 1H), 2.15 (m, 1H), 1.80 (m, 2H). MS (ESP+) m/z 365.17 (MH+), 387.17 (M+Na).

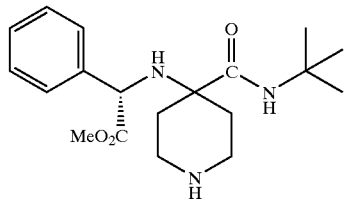

58% yield. MS (ESP+) m/z 368.24 (MH+).

H1 NMR (CDCl3, 300 MHz) δ 7.42–7.25 (m, 5H), 6.62 (s, 1H), 4.24 (d, 1H), 3.04 (dt, 1H), 2.93–2.70 (m, 5H), 2.20 (ddd, 1H), 1.90 (ddd, 1H), 1.10 (s, 9H).

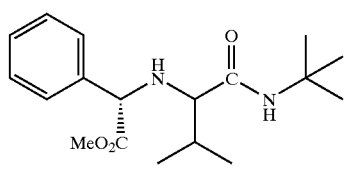

88% yield, ratio 2:1. MS (ESP+) m/z 321.26 (MH+), 343.22 (M+Na).

H1 NMR (CDCl3, 300 MHz, major diastereoisomer): δ 7.40–7.27 (m, 5H), 6.90 (s, 1H), 4.18 (s, 1H), 3.68 (s, 3H), 2.85 (d, 1H, 4.5 Hz), 2.12 (m, 1H), 1.21 (s, 9H), 1.04 (d, 3H, 6.9 Hz), 0.93 (d, 3H, 6.9 Hz).

H1 NMR (CDCl3, 300 MHz, minor diastereoisomer): δ 7.40–7.27 (m, 5H), 6.86 (s, 1H), 4.22 (s, 1H), 3.64 (s, 3H), 2.57 (d, 1H, 4.5 Hz), 2.02 (m, 1H), 1.37 (s, 9H), 0.85 (d, 3H, 6.9 Hz), 0.83 (d, 3H, 6.9 Hz).

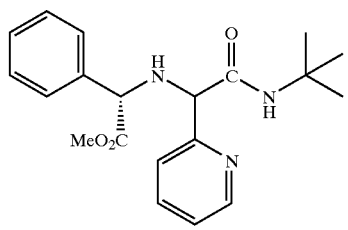

61% yield, ratio 4:3. MS (ESP+) m/z 356.21 (MH+), 378.17 (M+Na).

H1 NMR (CDCl3, 300 MHz, major diastereoisomer): δ 8.55 (m, 1H), 7.66 (m, 1H), 7.54 (m, 1H), 7.38–7.25 (m, 5H), 7.20 (m, 1H), 4.36 (s, 1H), 4.17 (s, 1H), 3.65 (s, 3H), 1.21 (s, 9H).

H1 NMR (CDCl3, 300 MHz, minor diastereoisomer): δ 8.50 (m, 1H), 7.59 (m, 1H), 7.47 (m, 1H), 7.38–7.25 (m, 5H), 7.16 (m, 1H), 4.44 (s, 1H), 4.06 (s, 1H), 3.69 (s, 3H), 1.32 (s, 9H).

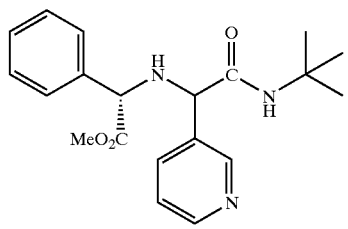

48% yield, ratio 3:2. MS (ESP+) m/z 356.67 (MH+), 378.19 (M+Na).

H1 NMR (CDCl3, 300 MHz, major diastereoisomer): δ 8.47 (d, 1H), 8.52 (dd, 1H), 7.68 (dt, 1H), 7.58 (dt, 1H), 7.39–7.21 (m, 5H), 6.99 (br s, 1H), 4.33 (s, 1H), 4.00 (s, 1H), 3.70 (s, 3H), 1.36 (s, 9H).

H1 NMR (CDCl₃, 300 MHz, minor diastereoisomer): δ 8.60 (d, 1H), 8.56 (dd, 1H), 7.49 (dt, 1H), 7.47 (dt, 1H), 7.39–7.21 (m, 5H), 7.01 (br s, 1H), 4.28 (s, 1H), 4.08 (s, 1H), 3.70 (s, 3H), 1.27 (s, 9H).

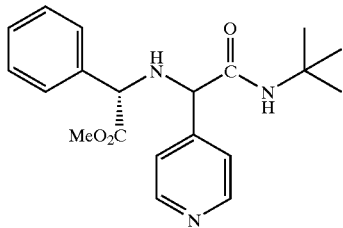

50% yield, ratio 1:1 MS (ESP+) m/z 356.24 (MH⁺), 378 (M+Na).

H1 NMR (CDCl3, 300 MHz, mixture of diastereoisomers): δ 8.59 and 8.53 (d, 1H, 6.1 Hz), 7.39–7.25 (m, 5H), 7.18 and 7.14 (d, 2H), 6.94 and 6.84 (br s, 1H), 4.31 and 4.27 (s, 1H), 4.04 and 3.97 (s, 1H), 3.71 (s, 3H), 1.34 and 1.25 (s, 9H).

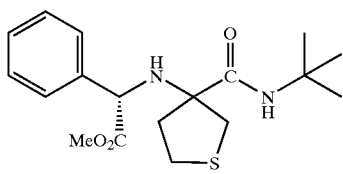

40% yield, ratio 1:1. MS (ESP+) m/z 351.13 (MH⁺), 373.12 (M+Na).

H1 NMR (CDCl3, 300 MHz): δ 7.43–7.23 (m, 5H), 4.23 and 4.20 (s, 1H), 3.67 and 3.66 (s, 3H), 3.21 (s, 2H), 3.03 (t, 2H, 7.2 Hz), 2.59 (t, 2H, 7.2 Hz), 1.13 and 1.02 (s, 9H).

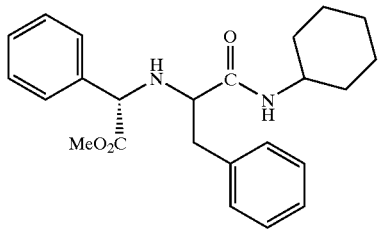

quantitative yield, ratio 1:1.

H1 NMR (CDCl3, 300 MHz): δ 7.42–7.08 (m, 8H), 6.89 (d, 2H), 4.20 (s, 1H), 3.67 and 3.60 (s, 3H), 3.40 and 3.12 (dd, 1H, 8.2–4.5 Hz), 3.26 and 3.20 (dd, 1H, 13.8–4.5), 2.89 and 2.68 (dd, 1H, 13.8–8.2 Hz), 1.99–0.85 (m, 10H).

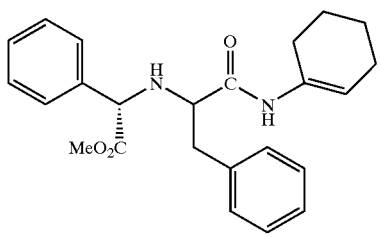

quantitative yield, ratio 2:1. MS (ESP+) m/z 393.19 (MH⁺), 415.17 (M+Na).

H1 NMR (CDCl3, 300 MHz, major diastereosiomer): δ 8.00 (s, 1H), 7.39–7.36 (m, 10H), 6.07 (m, 1H), 4.15 (s, 1H), 3.54 (s, 3H), 3.35 (dd, 1H, 8.6–4.0 Hz), 3.25 (dd, 1H, 13.7–4.0 Hz), 2.82 (dd, 1H, 13.7–8.6 Hz), 2.08 (m, 2H), 1.90 (m, 2H), 1.57 (m, 4H).

H1 NMR (CDCl3, 300 MHz, minor diastereosiomer): δ 8.35 (s, 1H), 7.27–7.03 (m, 8H), 6.78 (d, 2H0, 6.22 (m, 1H), 4.15 (s, 1H), 3.61 (s, 3H0, 3.20 (dd, 1H, 13.8–4.0 Hz), 3.08 (dd, 1H, 9.9–4.0 Hz), 2.61 (dd, 1H, 13.8–9.9 Hz), 2.15 (m, 3H), 1.78–1.56 (m, 5H).

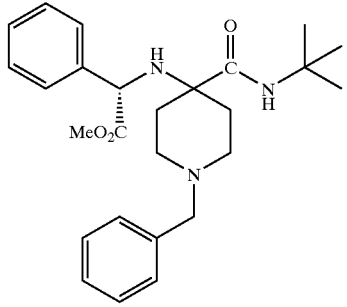

86% yield. MS (ESP+) m/z 438.65 (MH⁺).

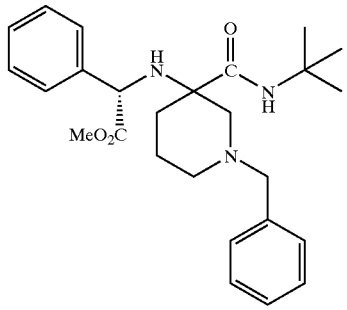

MS (ESP+) m/z 438.33.

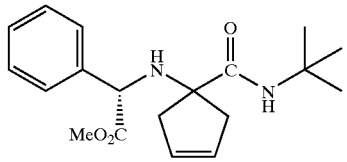

NMR, MS, IR and yield not determined.

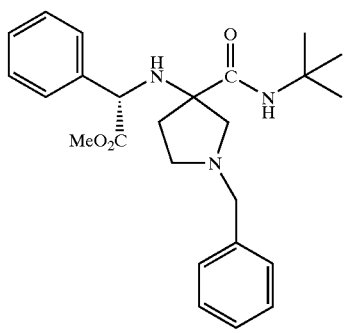

MS (ESP+) m/z 424.25 (MH⁺).

Example II

Preparation of Intermediary Compound of Formula 3 and Conversion Thereof Into Desired Compound of Formula 1

The respective compounds of Formula 3 were obtained according to Scheme 2 as follows:

Scheme 2

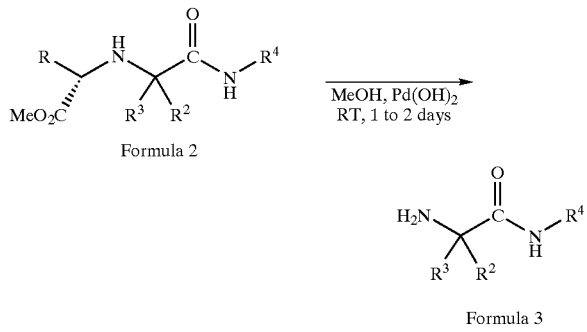

Formula 2

Formula 3

General Procedure

Several of the compounds of Formula 2 (made as shown above in Example I) were each respectively dissolved in MeOH (10 mL/mmol) and Pd(OH)$_2$ (0.2 to 0.8 eq) was added. Each respective mixture was degassed and H$_2$ gas was added. This procedure was repeated three times. Then, each respective mixture was allowed to stir under a H$_2$ atmosphere until the reaction was complete.

Each respective crude concentrate mixture was filtered through Celite™ and washed with MeOH (10 ml/mmol). Each respective filtrate was concentrated to lead to a crude.

Each respective crude concentrate was dissolved in Et$_2$O and washed with 2N HCl (10 mL/mmol) twice. The combined aqueous layers were basified to pH~8 by addition of K$_2$CO$_3$ solid, and then extracted with Et$_2$O (10 mL/mmol) twice. The combined organic layers were dried over Na$_2$SO$_4$ and concentrated to lead to the desired products of Formula 3 as follows:

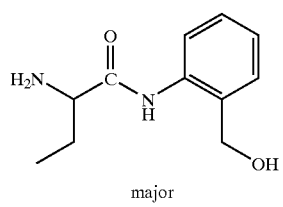

major

73% yield. MS (ESP+) m/z 231.17 (M+Na).

H1 NMR (CD$_3$OD, 300 MHz): δ 7.74 (d, 1H, 8.4 Hz), 7.38 (d, 1H, 8.4 Hz), 7.30 (td, 1H, 7.6–1.7 Hz), 7.17 (td, 1H, 7.6–1.7 Hz), 4.64 (s, 2H), 3.44 (dd, 1H, 6–6.6 Hz), 1.86 (m, 1H), 1.70 (m, 1H), 1.05 (t, 3H).

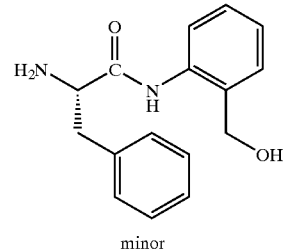

minor

57% yield.

H1 NMR (CD$_3$OD, 300 MHz): δ 7.67 (dd, 1H), 7.34–7.22 (m, 7H), 7.13 (td, 1H), 4.40 (s, 2H), 3.72 (dd, 1H, 7.6–6.1 Hz), 3.11 (dd, 1H, 13.4–6.1 Hz), 2.94 (dd, 1H, 13.4–7.6 Hz). MS (ESP+): m/z 271.04 (MH$^+$), 293.04 (M+Na).

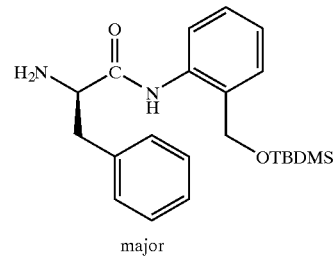

major

72% yield.

H1 NMR (CD$_3$OD, 300 MHz): δ 7.73 (d, 1H), 7.35–7.23 (m, 7H), 7.13 (td, 1H), 4.52 (s, 2H), 3.81 (dd, 1H, 7.2–6.4 Hz), 3.14 (dd, 1H, 13.3–6.4 Hz), 3.00 (dd, 1H, 13.3–7.2 Hz), 0.89 (s, 9H), 0.06(s, 3H), 0.03 (s, 3H). MS (ESP+): m/z 385.29 (MH$^+$), 407.30 (M+Na).

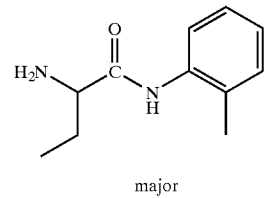

major

NMR, MS, IR and yield not determined.

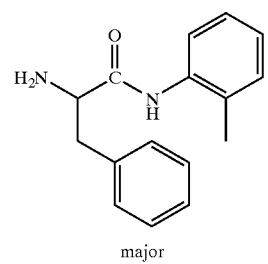

major

NMR, MS, IR and yield not determined.

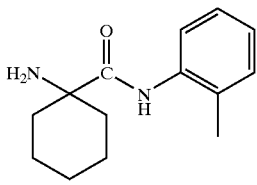

95% yield.

H1 NMR (CD₃OD, 300 MHz): δ 7.68 (dd, 1H, 8.1–0.9 Hz), 7.20 (d, 1H, 8.1), 7.16 (t, 1H, 8.1), 7.05 (dt, 1H, 8.1–0.9 Hz), 2.26 (s, 3H), 1.99 (m, 2H), 1.75–1.50 (m, 8H). MS (ESP+): m/z 233.10 (MH⁺).

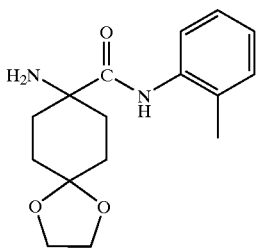

58% yield.

H1 NMR (CD₃OD, 300 MHz): δ 7.57 (d, 1H), 7.35–7.25 (m, 2H), 7.06 (td, 1H), 4.61 (m, 4H), 2.27 (m, 2H), 2.25 (s, 3H), 1.85 (m, 2H), 1.72 (m, 2H), 1.62 (m, 2H). MS (ESP+): m/z 291.07 (MH⁺).

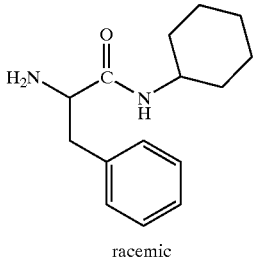

racemic

35% yield.

H1 NMR (CDCl3, 300 MHz, racemic): δ 7.34–7.19 (m, 5H), 3.74 (m, 1H), 3.56 (dd, 1H, 9.2–4.1 Hz), 3.23 (dd, 1H, 13.9–4.1 Hz), 2.90 (dd, 1H, 13.9–9.2 Hz), 1.85 (m, 2H), 1.68 (m, 2H), 1.6–1.07 (m, 6H).

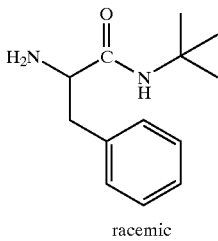

racemic

77% yield.

H1 NMR (CD₃OD, 300 MHz, racemic): δ 7.30–7.13 (m, 5H), 3.43 (m, 1H), 2.90 (dd, 1H), 2.77 (dd, 1H), 1.21 (s, 9H).

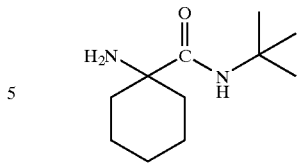

71% yield.

H1 NMR (CD₃OD, 300 MHz): δ 1.85 (m, 2H), 1.68–1.44 (m, 8H), 1.30 (s, 9H). MS (ESP+): m/z 199.22 (MH⁺), 221.21 (M+Na).

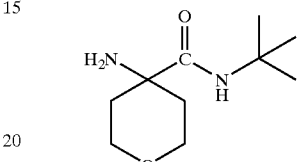

88% yield.

H1 NMR (CD₃OD, 300 MHz): δ 3.81–3.65 (m, 4H), 2.11 (m, 2H), 1.33 (s, 9H), 1.32 (m, 2H). MS (ESP+): m/z 201.22 (MH⁺), 233.19 (M+Na).

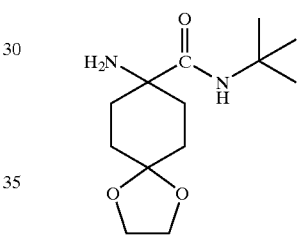

39% yield.

H1 NMR (CD₃OD, 300 MHz): δ 3.91 (m, 4H), 2.62 (m, 4H), 2.28 (m, 4H), 1.35 (s, 9H). MS (ESP+): m/z 257.15 (MH⁺).

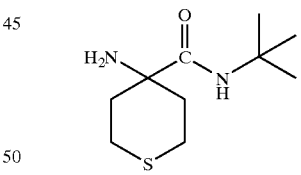

NMR, MS, IR and yield not determined.

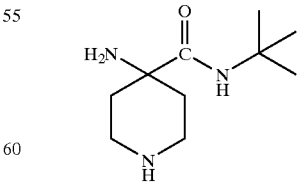

quantitative yield.

H1 NMR (CD₃OD, 300 MHz): δ 2.90–2.70 (m, 4H), 2.06 (ddd, 1H), 1.86 (ddd, 1H), 1.58 (m, 2H), 1.14 (s, 9H). MS (ESP+) m/z 200.06 (MH⁺).

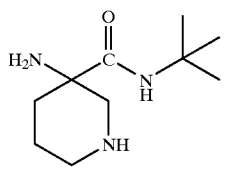

NMR, MS, IR and yield not determined.

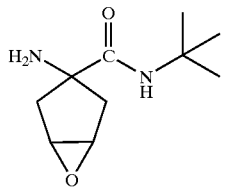

NMR, MS, IR and yield not determined.

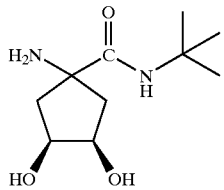

NMR, MS, IR and yield not determined.

Then the respective compounds of Formula 1 were obtained according to Scheme 3 as follows:

Scheme 3

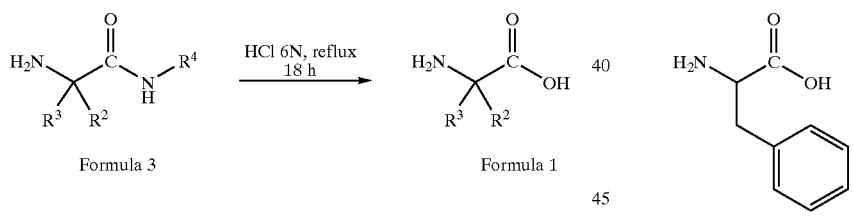

Formula 3                    Formula 1

General Procedure

To each respective compound of Formula 3 was added HCl 6N (10 mL/mmol) and the reaction mixture was stirred at reflux for 24 h. Next, each respective mixture was cooled to room temperature and extracted with ether (10 mL/mmol) twice. For each, the aqueous layer was then concentrated to afford the following desired alpha-amino acid compounds of Formula 1 in the form of the hydrochloride salt:

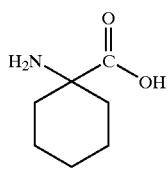

quantitative yield.

H1 NMR (CD$_3$OD, 300 MHz, HCl salt): δ 2.11 (m, 2H), 1.84–1.46 (m, 8H). MS (ESP+): m/z 144.19 (MH+).

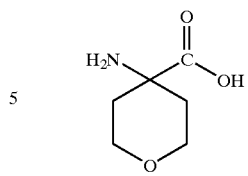

quantitative yield.

H1 NMR (CD$_3$OD, 300 MHz, HCl salt): δ 3.85 (m, 4H), 2.21 (m, 4H), 1.85 (m, 4H). MS (ESP+) m/z 146.02 (MH$^+$).

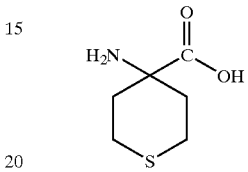

NMR, MS, IR and yield not determined.

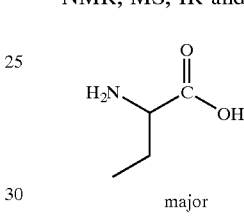

major quantitative yield.

H1 NMR (CD$_3$OD, 300 MHz, HCl salt): δ 3.93 (t, 1H, 6 Hz), 1.96 (m, 2H), 1.06 (t, 3H, 7.7 Hz). MS (ESP+) m/z 104.22 (MH$^+$).

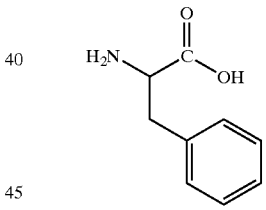

quantitative yield.

H1 NMR (CD$_3$OD, 300 MHz, racemic HCl salt): δ 7.41–7.25 (m, 5H), 4.25 (dd, 1H, 7.6–5 Hz), 3.31 (dd, 1H, 14.6–5 Hz), 3.14 (dd, 1H, 14.6–7.6 Hz).

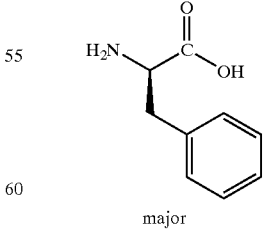

major

H1 NMR (CD$_3$OD, 300 MHz, HCl salt): δ 7.45–7.29 (m, 5H), 4.24 (dd, 1H, 7.5–5.4 Hz), 3.31 (dd, 1H, 14.2–5.4 Hz), 3.16 (dd, 1H, 14.2–7.5 Hz). MS (ESP+): m/z 165.97 (MH+). α$_D$=+12 (c=0.2, H$_2$O).

minor

87% yield.

H1 NMR (CD$_3$OD, 300 MHz, HCl salt): δ 7.40–7.26 (m, 5H), 4.26 (dd, 1H, 7.8–5.3 Hz), 3.31 (dd, 1H, 14.6–5.3), 3.14 (dd, 1H, 14.6–7.8 Hz). MS (ESP+) 166.00 (MH$^+$).

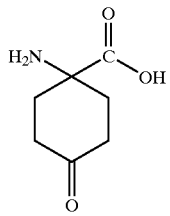

60% yield.

H1 NMR (CD$_3$OD, 300 MHz, HCl salt): δ 2.36–2.12 (m, 3H), 2.02–1.69 (m, 5H). MS (ESP+) m/z 155.05 (M−2).

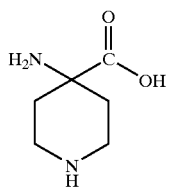

quantitative yield.

H1 NMR (CD$_3$OD, 300 MHz, HCl salt): δ 3.6–2.96 (m, 4H), 2.67–1.88 (m, 4H).

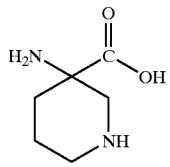

NMR, MS, IR and yield not determined.

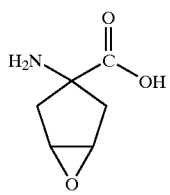

NMR, MS, IR and yield not determined.

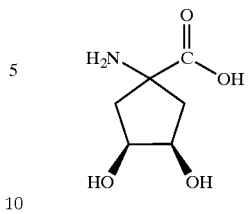

NMR, MS, IR and yield not determined.

Example III

Preparation of N-Protected Compound of Formula 1

N-Protection With Fmoc.

The respective N-protected compounds of Formula 1 were obtained according to Scheme 4 as follows:

Scheme 4

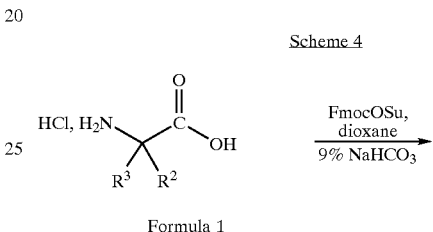

Formula 1

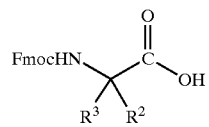

Formula 1 with Fmoc as N-protecting group

General Procedure

Several of the amino-acid compounds (HCl salt) of Formula 1 (made as shown above in Example II) were respectively dissolved in a solution of NaHCO$_3$ (10 mL/mmol) and a solution of FmocOSu in dioxan (10 mL/mmol) was added to each. Each mixture was stirred for 0.5 h and then diluted with H$_2$O and AcOEt (10 mL/mmol).

After extraction the aqueous layer for each was extracted with AcOEt (10 mL/mmol, twice). The combined organic layers were washed by H$_2$O (10 mL/mmol). The aqueous phase was acidified with a 2N HCl solution to pH-2 and extracted with AcOEt (10 mL/mmol, twice). The combined organic layers were dried over Na$_2$SO$_4$ and concentrated to lead to the desired products of N-protected Formula 1 as follows:

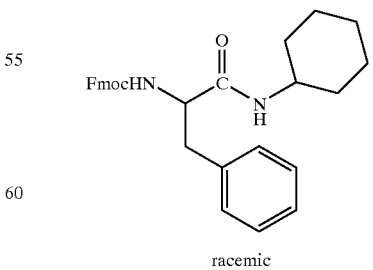

racemic

61% yield.

H1 NMR (CDCl3, 300 MHz, racemic): δ 7.76 (d, 2H, 7.8 Hz), 7.55 (d, 2H, 7.8 Hz), 7.40 (t, 2H, 7.8 Hz), 7.30 (dt, 2H, 7.8–1.4 Hz), 7.27–7.15 (m, 5H), 5.40 (br d, 1H), 4.42 (m, 2H), 4.29 (m, 1H), 4.19 (t, 1H), 1.87 (m, 1H),

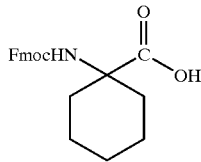

25% yield.

H1 NMR (CD₃OD, 300 MHz): δ 7.78 (d, 2H, 7.4 Hz), 7.68 (d, 2H, 7.4 Hz), 7.38 (dt, 2H, 7.4–1.4 Hz), 7.30 (dt, 2H, 7.4–1.4 Hz), 4.31 (d, 2H, 6.8 Hz), 4.21 (t, 1H, 6.8 Hz), 2.06 (m, 2H), 1.81 (m, 2H), 1.58 (m, 4H). MS (ESP+) m/z 366.14 (MH⁺).

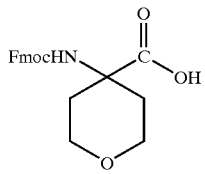

97% yield.

H1 NMR (CD₃OD, 300 MHz): δ 7.78 (d, 2H, 7.4 Hz), 7.67 (d, 2H, 7.4 Hz), 7.37 (dt, 2H, 7.4–1.3 Hz), 7.29 (dt, 2H, 7.4–1.3 Hz), 4.36 (br d, 2H, 6.2 Hz), 4.20 (t, 1H, 6.2 Hz), 3.74 (m, 2H), 3.60 (m, 2H), 2.08 (m, 2H), 1.95 (m, 2H). MS (ESP+) m/z 368.10 (MH⁺).

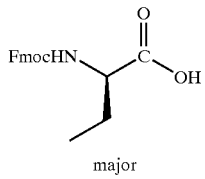

major

65% yield.

H1 NMR (CD₃OD, 300 MHz): δ 7.78 (d, 2H, 7.2 Hz), 7.66 (d, 2H), 7.37 (t, 2H), 7.29 (dt, 2H, 7.2–1.3 Hz), 4.34 (m, 2H), 4.22 (t, 1H, 7 Hz), 4.06 (dd, 1H, 5.6–9.6 Hz), 1.87 (m, 1H), 1.70 (m, 1H), 0.97 (t, 3H, 7.1 Hz). α_D=+18 (c=0.16, DMF). MS (ESP+) m/z 326.14 (MH⁺), 348.08 (M+Na).

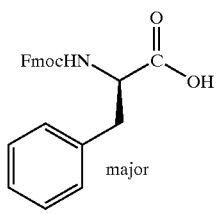

major

44% yield.

H1 NMR (CD₃OD, 300 MHz): δ 7.77 (d, 2H, 7.8 Hz), 7.58 (d, 2H, 7.8 Hz), 7.38 (t, 2H, 7.8 Hz), 7.31–7.14 (m, 6H), 4.41 (dd, 1H, 9.24.8 Hz), 4.34–4.10 (m, 3H), 3.20 (dd, 1H, 144.8 Hz), 2.93 (dd, 1H, 14–9.2 Hz). MS (ESP+) m/z 388.12 (MH⁺), 410.15 (M+Na).

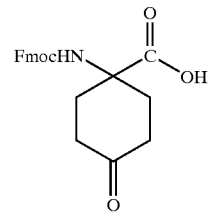

MS (ESP+) m/z 379.21.

N-Protection With BOC.

The respective N-protected compounds of Formula 1 were obtained according to Scheme 5 as follows:

Scheme 5

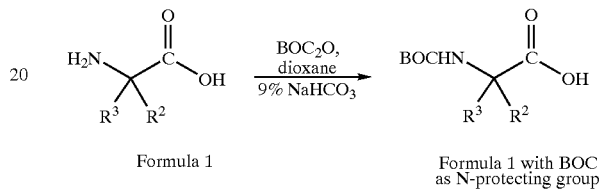

Formula 1                Formula 1 with BOC
                         as N-protecting group General Procedure Several of the amino-acid compounds (HCl salt) of Formula 1 (made as shown above in Example II) were respectively dissolved in a solution of NaHCO₃ (10 mL/mmol) and a solution of BOC₂O in dioxan (10 mL/mmol) was added to each. Each mixture was stirred for 0.5 h and then diluted with H₂O and AcOEt (10 mL/mmol).

After extraction the aqueous layer for each was extracted with AcOEt (10 mL/mmol, twice). The combined organic layers were washed by H₂O (10 mL/mmol). The aqueous phase was acidified with a 2N HCl solution to pH-2 to 4 and extracted with AcOEt (10 mL/mmol, twice). The combined organic layers were dried over Na₂SO₄ and concentrated to lead to the desired products of N-protected Formula 1 as follows:

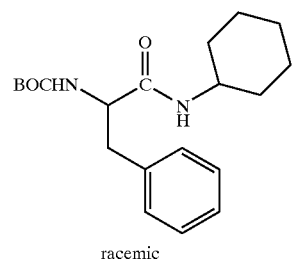

racemic

54% yield

H1 NMR (CDCl3, 300 MHz, racemic): δ 7.33–7.14 (m, 5H), 5.40 (br s, 1H), 5.10 (br s, 1H), 4.20 (dd, 1H, 8.6–5.8 Hz), 3.66 (m, 1H), 3.10 (dd, 1H, 13.2–5.8 Hz), 2.95 (dd, 1H, 13.2–8.6 Hz), 1.85–0.78 (m, 10H), 1.41 (s, 9H).

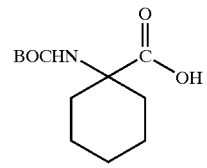

15% yield.

H1 NMR (CD$_3$OD, 300 MHz): δ 1.96 (m, 2H), 1.78 (m, 2H), 1.64–1.48 (m, 4H), 1.43 (s, 9H). MS (ESP+) m/z 266.11 (M+Na).

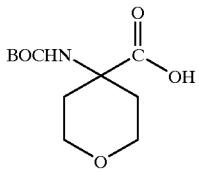

46% yield.

H1 NMR (CD$_3$OD, 300 MHz): δ 3.76 (dt, 2H, 11.9–4.0 Hz), 3.65 (td, 2H, 11.9–4.0 Hz), 2.07 (m, 2H), 1.92 (m, 2H), 1.42 (s, 9H). MS (ESP+) m/z 268.07 (M+Na).

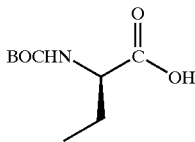

95% yield.

H1 NMR (CD$_3$OD, 300 MHz): δ 3.89 (dd, 1H, 8.2–4.8 Hz), 1.81 (m, 1H), 1.65 (m, 1H), 1.44 (s, 9H), 0.96 (t, 3H, 7.4 Hz). α$_D$=+13 (c=0.15, ethanol). MS (ESP+) m/z 226.02 (M+Na).

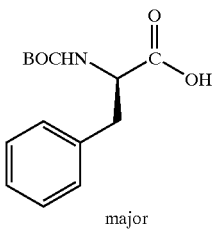

major

92% yield.

H1 NMR (CD$_3$OD, 300 MHz): δ 7.30–7.14 (m, 5H), 4.33 (dd, 1H, 9.1–5.1 Hz), 3.14 (dd, 1H, 13.3–5.1 Hz), 2.89 (dd, 1H, 13.3–9.1 Hz), 1.36 (s, 9H). α$_D$=−10 (c=0.2, Ethanol). MS (ESP+) m/z 288.11 (M+Na).

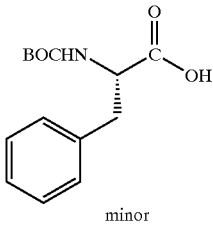

minor

32% yield.

H1 NMR (DMSO-d6, 300 MHz): δ 7.12–7.04 (m, 5H), 4.06 (m, 1H), 2.99 (m, 1H), 2.79 (m, 1H). MS (ESP+) m/z 258.05 (M+Na).

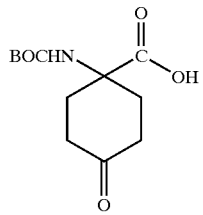

MS (ESP) m/z 258.05 (M+Na).

It will be understood that various details of the invention may be changed without departing from the scope of the invention. Furthermore, the above description is for the purpose of illustration only, and not for the purpose of limitation—the invention being defined by the claims.

What is claimed is:

1. A method for making a compound of Formula 1

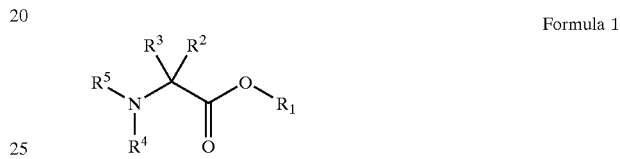

Formula 1 where R$^1$ is selected from:
  (a) H,
  (b) mono-, di-, and tri-substituted aryl, and
  (c) C$_1$–C$_{10}$ alkyl, C$_1$–C$_{10}$ substituted alkyl, C$_1$–C$_{10}$ substituted alkyl-aryl, C$_1$–C$_{10}$ substituted alkenyl, and C$_1$–C$_{10}$ substituted alkenyl aryl, and R$^2$ and R$^3$ are the same or different and are selected from
  (a) H, with the proviso that at least one of R$^2$ and R$^3$ is not H, and
  (b) C$_1$–C$_{10}$ alkyl, C$_1$–C$_{10}$ substituted alkyl, C$_1$–C$_{10}$ substituted alkyl-aryl, C$_1$–C$_{10}$ substituted alkenyl, and C$_1$–C$_{10}$ substituted alkenyl aryl, and
    wherein R$^2$ and R$^3$ may be joined together to form a cyclic or heterocyclic ring having a ring size of 3 to 8 members.

where the substituents of R$^1$, R$^2$, and R$^3$ are selected from:
  H, chloro, fluoro, bromo, iodo, nitro, cyano, amino, C$_1$–C$_{10}$ alkyloxy, C$_1$–C$_{10}$ alkyloxy aryl, C$_1$–C$_{10}$ aminoalkyl, C$_1$–C$_{10}$ alkylamino, C$_1$–C$_{10}$ aminoalkyl aryl, C$_1$–C$_{10}$ aminocarbonyl, C$_1$–C$_{10}$ aminocarbonylalkyl-aryl, C$_1$–C$_{10}$ thioalkyl, C$_1$–C$_{10}$ thioalkyl-aryl, C$_1$–C$_{10}$ alkylsulfoxide, C$_1$–C$_{10}$ alkylsulfone, C$_1$–C$_{10}$ alkylsulfonamide, C$_1$–C$_{10}$ alkylsulfonamide aryl, C$_1$–C$_{10}$ alkylsufoxide aryl, C$_1$–C$_{10}$ alkylsulfone aryl, C$_1$–C$_{10}$ alkyl, aminocarbonylamino C$_1$–C$_{10}$ alkyl, C$_1$–C$_{10}$ alky aminocarbonylamino C$_1$–C$_{10}$ alkyl aryl, C$_1$–C$_{10}$ alkyloxycarbonyl C$_1$–C$_{10}$ alkyl, C$_1$–C$_{10}$ alkyloxycarbonyl C$_1$–C$_{10}$ alkyl aryl, C$_1$–C$_{10}$ carboxyalkyl, C$_1$–C$_{10}$ carboxyalkyl aryl, C$_1$–C$_{10}$ carbonylalkyl, C$_1$–C$_{10}$ carbonylalkyl aryl, C$_1$–C$_{10}$ alkyloxcarbonylamino alkyl, C$_1$–C$_{10}$ alkyloxycarbonylamino alkyl aryl, guanidino, C$_1$–C$_{10}$ alkylCOOH, C$_1$–C$_{10}$ alkylCONH$_2$, C$_1$–C$_{10}$ alkenylCOOH, C$_1$–C$_{10}$ alkenyl CONH$_2$, and where the aryl group of R$^1$, R$^2$, and R$^3$ is selected from:
  phenyl, biphenyl, 2-napthyl, 1-napthyl, pyridyl, furyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, isoindolyl, purinyl, carbazolyl, isoxazolyl, thiazolyl, oxazolyl, benthiazolyl, benzoxazolyl; and where $R^4$ and $R^5$ are the same or different and are selected from:

(d) H, and (e) an amine protecting group; said method comprising:
  (i) reacting
    a amino acid of the formula $NH_2$—CHR—COOH or a salt thereof, wherein R is an aryl group selected from the group consisting of phenyl, biphenyl, 1-naphthyl, and 2-naphthyl, wherein the aryl group of R is substituted with 1 to 5 substituents selected from the group consisting of hydrogen, cyano, amino, $C_1$–$C_{10}$ alky, $C_1$–$C_{10}$ alkyloxy, $C_1$–$C_{10}$ alkyloxyarl, $C_1$–$C_{10}$ aminoalkyl, $C_1$–$C_{10}$ alkylamino, $C_1$–$C_{10}$ aminoalkyl aryl,
    a convertible isocyanide, and a compound of the formula $R^3$—CO—$R^2$, in an alcohol or an alcohol-containing solvent to obtain a compound of Formula 2

Formula 2 and (ii) subjecting the compound of Formula 2 to catalytic hydrogenation conditions, and to amide cleavage conditions, to obtain the compound of Formula 1.

2. The method of claim 1, where the amine protecting group of $R^4$ or $R^5$ is selected from phenyl, cyclohexenyl, cyclohexyl, t-butyl, 9-fluorenylmethylcarbonyl, tert-butyloxycarbonyl, allyloxycarbonyl, and benzyloxycarbonyl.

3. The method of claim 1, where the groups $R^2$ and $R^3$ are joined together to form cyclic compound with a ring system as represented by Formula 1a Formula 1a where the ring system has a ring size of 3 to 8 members.

4. The method of claim 3, where the ring system is selected from:

(a) mono-, di-, tri-, or tetra-substituted cyclopropyl, cyclobutyl, cyclopentyl, cyclohexyl, cycloheptyl, and cyclooctyl as shown in compounds of Formulae 1b and 1c Formula 1b Formula 1c (b) mono-, di-, tri-, or tetra-substituted cyclopropenyl, cyclobutenyl, cyclopentenyl, cyclohexenyl, cycloheptenyl, and cyclooctenyl as shown in compounds of Formula 1d Formula 1d (c) mono-, di-, tri- or tetra-substituted heterocyclic compounds of Formulae 1e and 1f, where A is O, S, SO, $SO_2$, NH, $SO_2NHR^8$, $NCONHR^8$, $NCOOR^8$, or $NR^8$, Formula 1e Formula 1f and where $R^6$, $R^7$, $R^8$, $R^9$ and $R^{10}$ of Formulae 1a–1f are the same or different and are selected from:

(d) H, (e) mono-, di-, and tri-substituted aryl, and (f) $C_1$–$C_{10}$ substituted alkyl, $C_1$–$C_{10}$-substituted alkylaryl $C_1$–$C_{10}$ substituted alkenyl, and $C_1$–$C_{10}$ substituted alkenyl aryl, where the substituents of (e) and (f) are selected from:
  H, chloro, fluoro, bromo, iodo, nitro, cyano, amino, $C_1$–$C_{10}$ alkyloxy, $C_1$–$C_{10}$ alkyloxy aryl, $C_1$–$C_{10}$ aminoalkyl, $C_1$–$C_{10}$ alkylamino, $C_1$–$C_{10}$ aminoalkyl aryl, $C_1$–$C_{10}$ aminocarbonyl, $C_1$–$C_{10}$ aminocarbonylalkyl-aryl, $C_1$–$C_{10}$ thioalkyl, $C_1$–$C_{10}$ thioalkyl-aryl, $C_1$–$C_{10}$ alkylsulfoxide, $C_1$–$C_{10}$ alkylsulfone, $C_1$–$C_{10}$ alkylsulfonamide, $C_1$–$C_{10}$ alkylsulfonamide aryl, $C_1$–$C_{10}$ alkylsulfoxide aryl, $C_1$–$C_{10}$ alkylsulfone aryl, $C_1$–$C_{10}$ alkyl, aminocarbonylamino $C_1$–$C_{10}$ alkyl, $C_1$–$C_{10}$ alkyl aminocarbonylamino $C_1$–$C_{10}$ alkyl aryl, $C_1$–$C_{10}$ alkyloxycarbonyl $C_1$–$C_{10}$ alkyl, $C_1$–$C_{10}$ alkyloxycarbonyl $C_1$–$C_{10}$ alkyl aryl, $C_1$–$C_{10}$ carboxyalkyl, carboxyalkyl aryl, $C_1$–$C_{10}$ carbonylalkyl, $C_1$–$C_{10}$ carbonylalkyl aryl, $C_1$–$C_{10}$ alkyloxycarbonylamino alkyl, $C_1$–$C_{10}$ alkyloxcarbonylamino alkyl aryl, guanidino, $C_1$–$C_{10}$ alkylCOOH, $C_1$–$C_{10}$ alkylCONH$_2$, $C_1$–$C_{10}$ alkenylCOOH, $C_1$–$C_{10}$ alkenyl CONH$_2$, and where the aryl group of (e) and (f) are selected from: phenyl, biphenyl, 2-napthyl, 1-napthyl, pyridyl, furyl, thiophenyl, indolyl, isothiazolyl, imidazolyl, benzimidazolyl, tetrazolyl, pyrazinyl, pynimidyl, quinolyl, isoquinolyl, benzofuryl, isobenzofuryl, benzothienyl, pyrazolyl, isoindolyl, purinyl, carbazolyl, isoxazolyl, thiazolyl, oxazolyl, benthiazolyl, and benzoxazolyl.

5. The method of claim 1, where the amino acid is phenyl glycine, the convertible isocyanide is cyclohexenyl, tert-butyl, cyclohexyl, phenyl, or 2-(tert-butyldimethylsilyloxy methyl) phenyl isocyanides, the alcohol is methanol, ethanol, or isopropanol, and the catalytic hydrogenation conditions employ Pd(OH)$_2$ for a catalyst.

6. The method of claim 1, further comprising the step of attaching at least one amine protecting group on the amine of Formula 1.

7. The method of claim 1, where Formula 1 comprises a compound selected from the group consisting of:

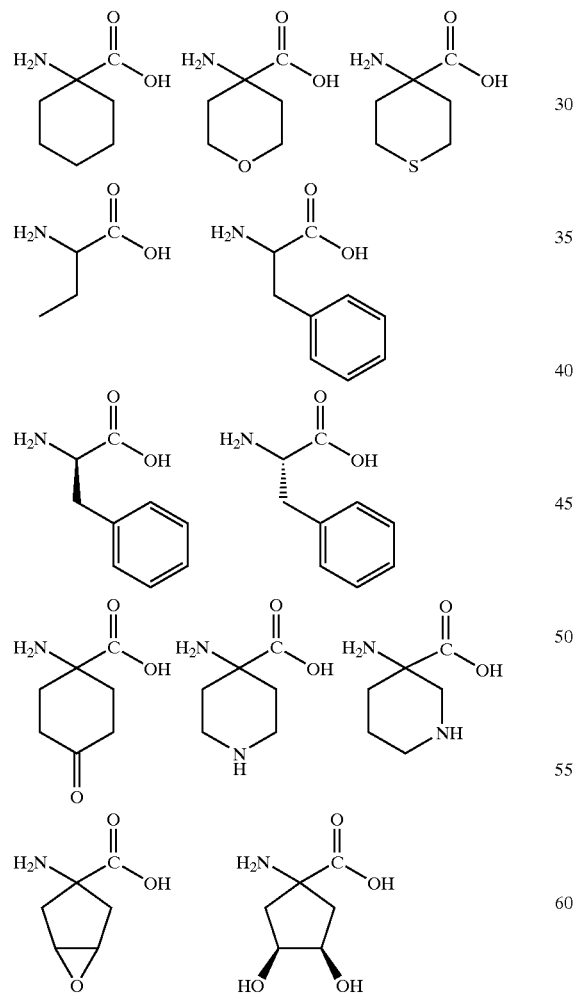

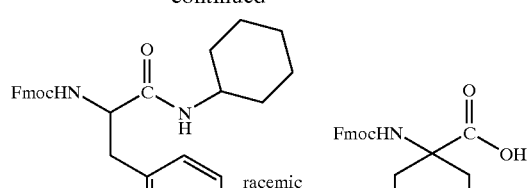

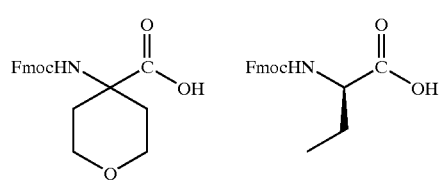

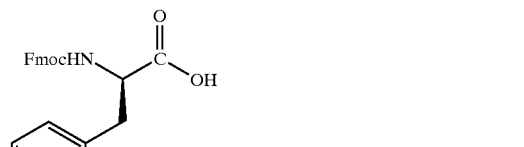

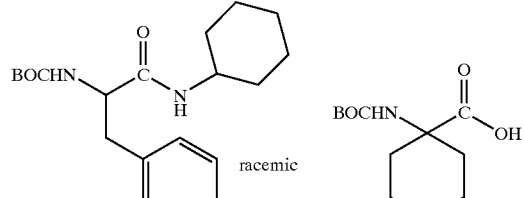

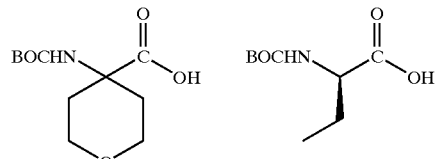

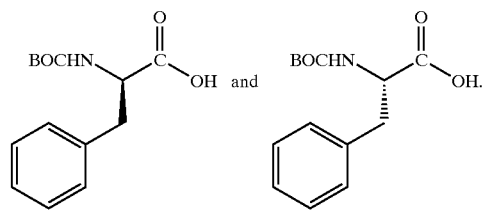

* * * * *